United States Patent
Boehm et al.

(10) Patent No.: US 8,656,782 B2
(45) Date of Patent: Feb. 25, 2014

(54) METHOD AND DEVICE FOR NON-DESTRUCTIVE MATERIAL TESTING OF A TEST OBJECT USING ULTRASONIC WAVES

(75) Inventors: Rainer Boehm, Berlin (DE); Matthias Goldammer, München (DE); Werner Heinrich, Oberkrämer Ot Bärenklau (DE)

(73) Assignee: Siemens Aktiengesellschaft, Munich (DE)

( * ) Notice: Subject to any disclaimer, the term of this patent is extended or adjusted under 35 U.S.C. 154(b) by 528 days.

(21) Appl. No.: 12/599,993

(22) PCT Filed: Apr. 4, 2008

(86) PCT No.: PCT/EP2008/054093
§ 371 (c)(1),
(2), (4) Date: Nov. 22, 2011

(87) PCT Pub. No.: WO2008/138684
PCT Pub. Date: Nov. 20, 2008

(65) Prior Publication Data
US 2012/0055252 A1 Mar. 8, 2012

(30) Foreign Application Priority Data

Mar. 15, 2007 (DE) .......................... 10 2007 022 981

(51) Int. Cl.
*G01N 29/04* (2006.01)
(52) U.S. Cl.
USPC .................................. 73/620; 73/602; 73/626
(58) Field of Classification Search
USPC ............ 73/620, 622, 624, 625, 626–628, 602
See application file for complete search history.

(56) References Cited

U.S. PATENT DOCUMENTS 3,952,581 A * 4/1976 Gottelt ............................ 73/640
4,131,026 A * 12/1978 Ries et al. ....................... 73/625
(Continued)

FOREIGN PATENT DOCUMENTS

| CN | 1409821 A | 4/2003 |
| CN | 1570620 A | 1/2005 |

(Continued)

OTHER PUBLICATIONS

Spies M et al: "Synthetic aperture focusing for defect reconstruction in anisotropic media", Ultrasonics, IPC Science and Technology Press Ltd. Guildford, GB, vol. 41, No. 2, Mar. 1 2003 pp. 125-131, 'XP004404920, ISSN: 0041-624X.

(Continued)

*Primary Examiner* — J M Saint Surin

(57) ABSTRACT

A method for the non-destructive material testing of a test object at least solid in some regions by subjecting the test object to ultrasonic waves and capturing the ultrasonic waves reflected within the test object. The method includes the steps, computer-supported dividing of the test object into a prescribed number of volume elements, subjecting the test object to ultrasound on a plurality of surface elements while probing the surface or at least one surface segment of the test object, capturing the sound waves reflected at the volume element while probing the plurality of surface elements on the surface or at least the surface segment of the test object, and in-phase addition of the sound waves reflected at the same volume elements and captured at various surface elements of the surface of the test object. Angle-dependent amplitude distribution is used in the sound field of the test head.

19 Claims, 3 Drawing Sheets

(56) References Cited

U.S. PATENT DOCUMENTS

| | | | |
|---|---|---|---|
| 4,235,112 A * | 11/1980 | Kaiser | 73/634 |
| 4,279,158 A | 7/1981 | Kajiyama et al. | |
| 4,524,622 A | 6/1985 | Suzuki et al. | |
| 4,576,034 A * | 3/1986 | Ferree et al. | 73/1.84 |
| 5,165,280 A * | 11/1992 | Sternberg et al. | 73/622 |
| 5,485,751 A * | 1/1996 | Karbach et al. | 73/618 |
| 5,801,312 A * | 9/1998 | Lorraine et al. | 73/602 |
| 6,487,909 B2 * | 12/2002 | Harrold et al. | 73/593 |
| 7,415,882 B2 * | 8/2008 | Fetzer et al. | 73/634 |
| 8,365,600 B2 * | 2/2013 | Kroning et al. | 73/602 |
| 2004/0123665 A1 | 7/2004 | Blodgett et al. | |

FOREIGN PATENT DOCUMENTS

| | | |
|---|---|---|
| EP | 0965839 A1 | 12/1999 |
| GB | 1001857 A | 8/1965 |
| JP | 55018987 A | 2/1980 |
| RU | 2037819 C1 | 6/1995 |
| RU | 2160893 C1 | 12/2000 |
| RU | 2280863 C1 | 7/2006 |
| WO | WO 2007024000 A1 | 3/2007 |

OTHER PUBLICATIONS

Ahmed Yamani: "Three-Dimensional Imaging Using a New Synthetic Aperture Focusing Technique" IEEE Transactions on Ultrasonics, Ferroelectrics Andfrequency, Control IEEE, Service Center, Piscataway, NJ, US, Band 44 , No. 4, Jul. 1, 1997, pp. 943-947, XP011090011, ISSN : 0885-3010.

Deutsch V et al: "3.4.3.6 Rechnergestützte Fehlerbeschreibung" Ultraschallpruefung: Grundlagen Und Industrielle Anwendungen, Jan. 1, 1997, pp. 133-141, XP0022787J6.

Deutsch V et al: "3.4 Fehlernachweis Und Gerätejustierung", Ultraschallprüfung ; Grundlagen Und Industrielle Anwendungen, Jan. 1, 1997, pp. 80-133, XP002280036.

* cited by examiner

METHOD AND DEVICE FOR NON-DESTRUCTIVE MATERIAL TESTING OF A TEST OBJECT USING ULTRASONIC WAVES

CROSS REFERENCE TO RELATED APPLICATIONS

This application is the US National Stage of International Application No. PCT/EP2008/054093, filed Apr. 4, 2008 and claims the benefit thereof. The International Application claims the benefits of German application No. 10 2007 022 981.1 DE filed May 15, 2007, both of the applications are incorporated by reference herein in their entirety.

FIELD OF INVENTION

The invention relates to a method for nondestructive material testing in accordance with the claims. The invention also relates to a corresponding device as claimed in the claims.

BACKGROUND OF INVENTION

It is necessary to examine for material defects the internal structure of numerous solid and partially solid products as well as intermediate products. To this end, there is a need for nondestructive test methods that provide information relating to the internal, invisible structure. This is required for mechanically highly stressed components, in particular.

For example, components made from steel are forged after being cast, and are subsequently brought into the final shape by turning. In this process, the testing for internal material defects can be performed as early as after the forging.

Such metal parts are usually tested with ultrasound. Sound waves that are reflected at interfaces in the material are detected in this case. The travel time of the reflected sound wave can be used to determine the path length it has covered. Further information relating to the material defect or defects can be obtained by insonification from various directions. Material defects can be located therefrom, by way of example. The geometric alignment of the material defect can be determined in this way, for example. Conclusions on the type of the material defect can be drawn from the shape of the reflected sound waves.

The volume accessible to the ultrasound can be completely investigated by scanning the surface of the test object with an ultrasonic detector and recording the data detected. An image can be generated from the detected data and be used for evaluation.

There are a number of options for determining the size of material defects. For example, the extent of the material defect can be read off directly during scanning. However, this requires the spatial resolution being smaller than the spatial extent of the material defect. The spatial resolution is limited by the wavelength used and the size of the aperture and therefore also by the diffraction of the sound waves.

The size of the material defect can also be determined with the aid of the amplitude of the reflected signal. It is thereby also possible to determine the size of such material defects as are smaller than the spatial resolution of the method. However, the amplitude of the reflected signal is also a function of further parameters, for example the orientation of the material defect, or the reflection properties at the interface.

The amplitude of the reflected signal decreases with decreasing size of the material defect. In this case, the spacing of the interference signals becomes too small to be able to identify the material defect from a single amplitude/travel time diagram. A spacing of +6 dB is expediently required between the measurement signal and the interference signal.

The spatial resolution can be optimized by focusing the sound waves with the aid of suitable test heads. In this process, the focusing can become narrower the wider the test head in relation to the wavelength. The focusing effects a higher sound pressure.

FIG. 4 shows a schematic sectional view of a test object 10 with a material defect 30. Located on the outside of the test object 10 is a test head 16 that is designed as a focusing test head. The test head 16 emits focused sound waves 32, 34 and 36. Here, the continuous line represents the wave front of the current sound wave 32. The dashed lines represent the wave fronts of the earlier sound waves 34 and the later sound waves 36. The focused sound waves 32, 34 and 36 propagate along a predetermined direction with a laterally bounded extent.

During scanning, the test head 16 moves on the surface of the test object 10 along a scanning direction 38. However, the focusing occurs only inside the near field of the test head 16. The larger the width of the test head 16 perpendicular to the scanning direction, the greater can be the distance of the detectable material defect 30.

One possibility for assessing the material defects is to evaluate the amplitude using the spacing/gain/size method (AVG method). Starting from the amplitude, the material defect is assigned an equivalent reflector size that would produce a vertically insonified free circular surface. When the detected signal is substantially greater than the interference signal or noise signal, there is no problem in evaluating the amplitude using the AVG method. In this case, the reflector must be located on the acoustic axis of the sound field of the test head 16. From the dependence of the amplitude on the spacing from the test head 16, the detected amplitude corresponds to a reflector size with known geometry and orientation relative to the acoustic axis. If, by contrast, the detected amplitude is smaller than the noise signal or of a comparable order of magnitude, the material defect cannot be identified from the amplitude/travel time diagram.

Another method for improving the spatial resolution is the synthetic aperture focus technique (SAFT), in which use is made of a small, nonfocusing test head. Here, a three-dimensional image of the test object is calculated with the aid of a two-dimensional mechanical scanning of the test object.

A schematic sectional view of a test object 10 with a material defect 30 is illustrated in FIG. 5 for the purpose of explaining the SAFT method. The test head 16 is located on the outside of the test object 10. By comparison with FIG. 4, the test head has a relatively small diameter and is not of focusing design. Spherical sound waves 42, 44 and 46 are emitted by the test head 16. The wave front of the current spherical sound wave 42 is illustrated by a continuous line. The dashed lines represent the wave fronts of the earlier spherical sound waves 44 and of the later spherical sound waves 46. A comparison of FIG. 4 and FIG. 5 makes clear that the wave fronts 32, 34 and 36 of the focused sound waves, on the one hand and the wave fronts 42, 44 and 46 of the spherical sound waves, on the other hand, are oppositely curved.

In the case of the SAFT method, the test object 10 is subdivided into volume elements by a computer. Each volume element is successively regarded as a reflector during scanning. The reflected signal components from various positions of the test head 16 which belong to the same volume element are recorded and added up in phase with the aid of the computer. In this way, echo signals of large amplitude are obtained on the basis of constructive interference only for such locations as have actual reflection. The echo signals are extinguished on the basis of destructive interference for locations without actual reflection. In the case of constructive interference, the scanning and computing operation simulates an ultrasonic detector whose size corresponds to the scanned surface and which is focused onto a location.

It is possible to determine therefrom the position of the material defect and, in the event of an extended material defect, also to determine the size thereof within the scope of the resolution. The accuracy is approximately comparable to that in the scanned region in the case of the above-named method, which uses the focused sound waves. With the SAFT method, the spatial resolution is not limited by the dimensions of the test head 16, and so a high spatial resolution is possible.

With the SAFT method, all the reflected signal components coming into consideration in each pixel in the expected defect region are added with a time shift that the signal components would have if the pixel were the source of a reflected wave. The time shift that corresponds to the phase angle results from the geometric relationships between the test head 16 and the pixel, particularly from the spacing between the test head 16 and the pixel. If the pixel is now actually the source of a reflected wave, the amplitude then increases at this site with the number of the various positions of the test head 16 from which the material defect was detected. For all other pixels, the phases do not correspond, and so the sum vanishes in an ideal case, but is at least very small.

The SAFT method is mostly used in order to achieve a high spatial resolution. In principle, this is a focusing method in which the limit of resolution results from the wavelength and the synthetic aperture. The synthetic aperture is determined by the angular range from which the material defect is detected. The aperture is limited by the movement of the test head 16 and the divergence of the sound field.

The test object can, by way of example, be a rotor of a gas or steam turbine that is used, in particular, for power generation. Such a rotor is exposed to high stress during operation. The speed of the rotor corresponds to the line frequency of the respective network. For example, a speed of 3000 revolutions per minute is required for a network with a line frequency of 50 Hz. Large centrifugal forces occur on the rotor in the case of such high speeds. The centrifugal forces increase with the diameter of the rotor. The larger the turbine is designed, the stronger also are the centrifugal forces.

When the turbine is started, the rotors are, in particular, strongly loaded thermally in a tangential direction. In this phase, the rotor is firstly cold and is brought up to operating temperature from the outside inward by the hot combustion gases. Consequently, the number of the starts is of particular significance for the lifetime of the turbine. The tangential loading is greatest for the rotor in the region of its central bore. Consequently, material defects in the vicinity of the bore have a decisive influence on the longevity of the turbines. Particularly in the coming generation of turbine wheel disks, there is a need for a clear increase in the detection sensitivity for axially/radially oriented material defects. A sufficiently accurate determination of the axially/radially oriented material defects is impossible with the test methods to date.

Because of the higher powers of the recent gas or steam turbines, there is a rise in requirements for the rotor to be free from material defects. The size of the rotors is also increasing, and this entails longer ultrasonic paths in the case of material testing. The minimum value of the detectable material defects increases in the inner region of the rotor owing to the larger path length of the ultrasound. There is thus a need for a method that can also enable material defects to be determined in large components.

SUMMARY OF INVENTION

It is an object of the invention to make available an improved method for finding and/or identifying material defects in a test object that enables material defects to be determined with sufficient accuracy even in the case of relatively large test objects.

This object is achieved by the subject matter in accordance with the claims.

It is provided in accordance with the invention to make use of an angle-dependent amplitude distribution in the sound field of the test head.

The core of the invention resides in a modified SAFT method in which consideration is given to the angle-dependent amplitude distribution in the sound field of the test head. It is possible in this way to consider different sensitivities that depend on the angle. The amplitudes of the individual reflected signals depend on the amplitude distribution in the sound field of the test head. The spatial sound pressure distribution of the test head is used for the purpose of determining the amplitudes of the reflected sound waves as well. In the conventional SAFT method, information relating to amplitude is lost.

By way of example, the angle-dependent amplitude distribution is used to determine a correction factor that corresponds to the mean sensitivity along the path through the sound field of the test head. The correction factor is determined by integrating over the amplitude distribution of the test head.

The amplitudes of the sound waves are preferably added up in phase within a predetermined angular interval about the acoustic axis. It is also possible to make use in this process of a test head with a small sound beam divergence, for example 3° to 5° at −6 dB.

Furthermore, the application of ultrasound to the test object can be performed at various insonification angles with reference to the surface element on the surface of the test object. Since material defects often have a preferred direction of extent, it is possible in accordance with the invention to adapt the scanning of the surface of the test object and the variation in the insonification angles to the geometry of the test object and the alignment of the material defects.

By way of example, the insonification angles lie within a cone whose axis of symmetry forms the normal to the respective surface element.

In a specific embodiment, it can be provided that the surface or at least the surface section of the test object is scanned along a predetermined line. Because of the various insonification angles, the volume of the test object can be completely detected without scanning the entire surface.

The surface or at least the surface section of the test object is preferably scanned in a rasterized fashion in accordance with a predetermined scheme. This scheme can be adapted to the geometry of the test object and/or of the material defect.

Furthermore, the surface or at least the surface section of the test object can also be completely scanned.

By way of example, the insonification angles are between 0° and 50°, preferably between 0° and 30°.

In particular, the method can be provided for an at least sectionally rotationally symmetrical test object. In this case, it is particularly easy to adapt the scanning to the geometry of the test object. This is so, in particular, when the method is provided for at an least sectionally cylindrical test body.

In this case, the insonification direction preferably has a radial, tangential and/or axial component with reference to the surface of the cylindrical test object. It is thereby possible, in particular, also to detect material defects of flat configuration.

In the preferred embodiment, the method is provided for material testing of a test object made from metal, in particular for material testing of a forged component. The method is particularly suitable for material testing of a turbine wheel.

The invention further relates to a device for nondestructive material testing of an at least sectionally solid test object, which is provided for the abovedescribed method.

The device preferably comprises at least one test head for the emission of ultrasonic waves and for the detection of the ultrasonic waves reflected inside the test object.

In particular, the test head is swivel mounted such that the insonification direction can be varied with reference to the surface normal to the surface of the test object.

Finally, the test head is mounted to swivel between 0° and 60°, preferably between 0° and 30°, with reference to the surface normal to the surface of the test object.

Further features, advantages and particular embodiments of the invention are the subject matter of the subclaims.

BRIEF DESCRIPTION OF THE DRAWINGS

The method in accordance with the invention is explained in more detail below in the description of the figures with the aid of preferred embodiments and with reference to the attached drawings, in which.

DETAILED DESCRIPTION OF INVENTION

Figure 1:
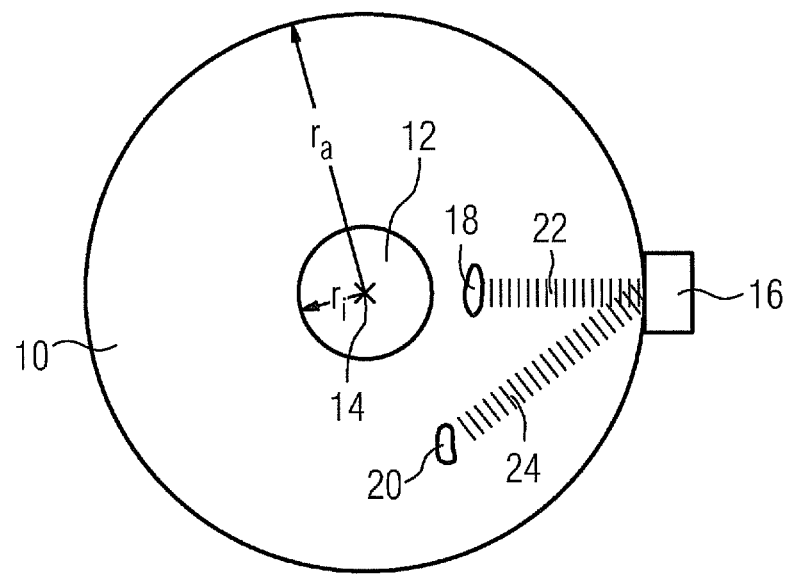
FIG. 1 shows a schematic lateral sectional view of a test object and of a test head in accordance with a preferred embodiment of the inventive method.

FIG. 1 shows a schematic sectional view of a test object 10. The test object 10 is of cylindrical design. The test object 10 has a bore 12 that is aligned concentrically with the test object 10. The bore 12 and the test object 10 therefore have a common axis of rotational symmetry 14, which extends in FIG. 1 in a fashion perpendicular to the plane of the drawing. The test object 10 has an outside radius $r_a$ and an inside radius $r_i$. The inside radius $r_i$ of the test object 10 therefore corresponds to the radius of the bore 12. In this particular embodiment, the test object 10 is a turbine disk for a gas or steam turbine.

A test head 16 is located on the lateral surface of the test object 10. The test head 16 comprises an ultrasonic transmitter and an ultrasonic detector. A tangential material defect 18 and a radial material defect 20 are also illustrated in the test object 10. The material defects 18 and 20 respectively form a cavity in the test object 10. The tangential material defect 18 substantially extends in a tangential direction with reference to the cylindrical test object 10. The radial material defect 20 correspondingly extends substantially in a radial direction with reference to the test object 10.

Material testing is performed by moving the test head 16 on the outer surface of the test object 10. FIG. 1 illustrates that a radial sound wave 22 is reflected particularly strongly at the tangential material defect 18, since the tangential material defect 18 is aligned substantially parallel to the surface of the test object 10. It is likewise made clear that a tangential sound wave 24 is reflected particularly intensively at the radial material defect 18.

It is made clear conversely that the tangential sound wave 24 would be reflected only very weakly at the tangential material defect 18. Again, the radial sound wave 22 would be reflected only slightly at the radial material defect 20.

In the inventive method, the insonification of the signal from the test head 16 is performed at various angles. In this case, either the test head 16 itself or at least its component emitting sound are swivel mounted in such a way that the entire volume of the test object 10 is accessible by scanning the outer circumferential surface. Consequently, in particular, those material defects 20 whose extent parallel to the surface of the test object 10 is relatively slight are detected more easily. By way of example, this is achieved in the case of the cylindrical test object 10 by virtue of the fact that in addition to the radial component the insonification direction also has a tangential component. Again, an insonification direction with a radial and an axial component would be possible. Finally, the insonification direction can also be composed of a radial, tangential and axial component.

In the method according to the invention, there is no imperative need for the entire surface or the entire surface section to be scanned in order to detect the total volume of the test object 10. For example, it is possible to scan a specific segment or a specific path of the surface since, owing to the swiveling of the test head 16, it is possible to detect at least the relevant region of the volume even without completely scanning the surface.

Figure 2:
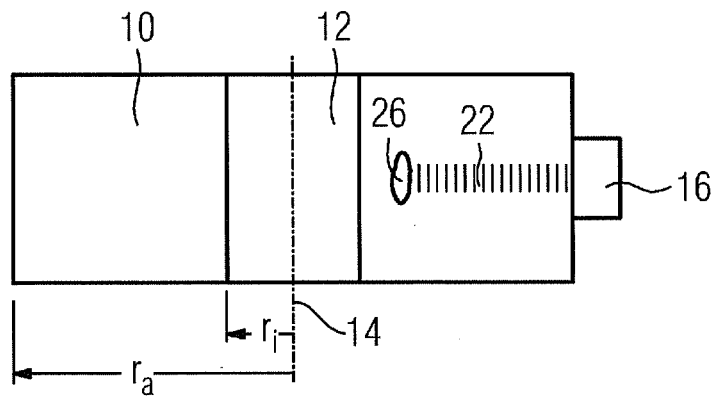
FIG. 2 shows a schematic sectional view from above of the test object and the test head in accordance with the preferred embodiment of the inventive method.

FIG. 2 illustrates a schematic sectional view from above of the test object 10 and the test head 16 in accordance with the embodiment in FIG. 1. FIG. 2 shows the bore 12, the axis of rotation of symmetry 14 and the radial sound wave 22. The axial material defect 26 is of sufficiently large extent, at least in an axial direction. FIG. 2 illustrates that the radial sound wave 22 is reflected sufficiently strongly by the axial material defect 26. Again, the tangential sound wave 24 would be sufficiently strongly reflected by the axial material defect 26 given a not excessively large insonification angle.

Figure 3:
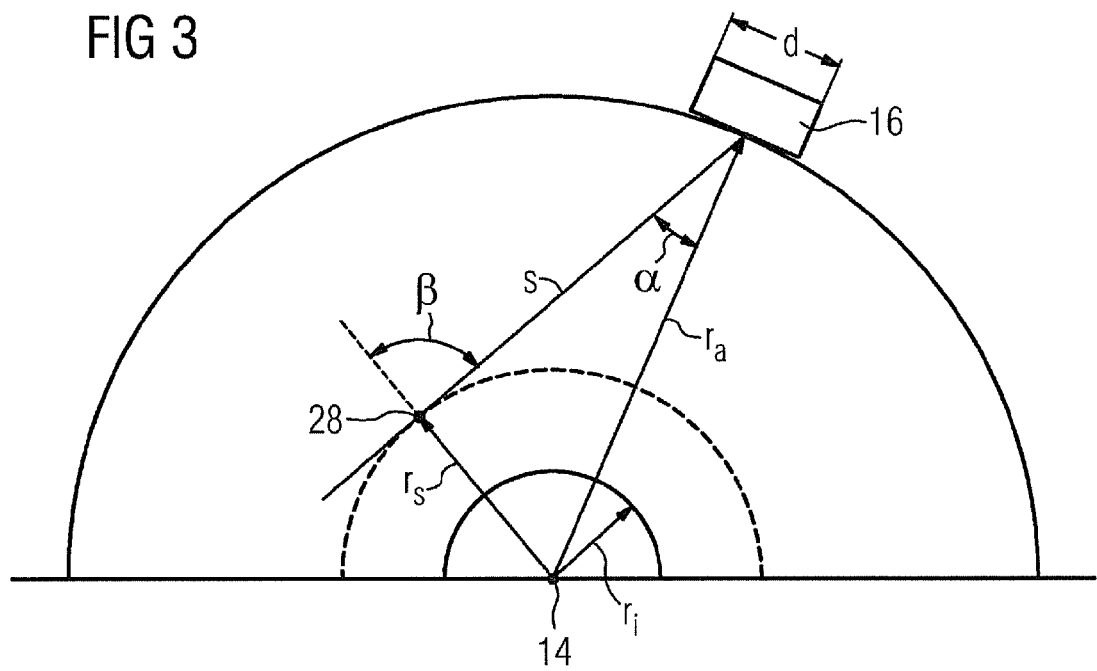
FIG. 3 shows a schematic of the geometric relationships of the test object, the test head and a material defect in the case of the preferred embodiment of the inventive method.

FIG. 3 shows a schematic of the geometric relationships of the test object 10, the test head 16 and a material defect 28 for the preferred embodiment of the inventive method. A radial spacing $r_s$ is defined between the material defect 28 and the axis of rotation of symmetry 14. The sound path s from the test head 16 up to the material defect 28 is given by:

$$s = \sqrt{(r_a^2 - r_i^2)}.$$

The angle between the sound path s and the surface normal $r_a$ forms the insonification angle α or the insonification direction. The sound path s and the corresponding spacing vector $r_s$ of the material defect 28 form a right angle β.

The use of the focusing test head 16 increases the sound pressure in the vicinity of the material defect 28. Consequently, the signal-to-noise ratio is improved. However, this is sensible only in the near field. The length n of the near field is given by:

$$n = d^2/(4\lambda).$$

Here, d is the width of the test head 16 and λ, is the wavelength of the sound wave. For a typical wavelength of λ=5 mm and a desired length of n=1 m for the near field, a test head 16 is required which has a width of d=140 mm. This near field length n can be achieved even without this width by using the SAFT method. In the SAFT method, a wide test head is simulated, thus achieving virtual focusing.

The amplitude of the reflected sound wave is dependent, on the one hand, on the spatial extent of the material defect 28 and, on the other hand, on the reflection properties at the interface of the material defect 28.

Two types of noise signals typically occur in the case of ultrasonic measurement. The first noise signal is that noise which occurs in every electronic detection system, in particular in the amplifiers. This can be reduced by averaging. There is no correlation between the first noise signal and the reflected sound signal, in particular no phase correlation. The summing of the signals therefore leads to an averaging of the noise signals With an increasing number of summands, the sum of these noise signals vanishes when the noise signals contain no direct voltage component. In practice, either no or only a slight direct voltage component occurs.

The second noise signal comes from the test object itself. The reflections at the microstructure of the metal form a noise carpet that correlates with the reflected sound signal. The noise carpet is likewise a reflected sound signal. It is produced by reflections in polycrystalline materials at grain boundaries thereof and in regions of different orientation of the crystal axes. Crystals are acoustically anisotropic, and so the wave resistance changes at the grain boundaries. This affects all metal materials in practice. The individual reflections owing to the microstructure cause no interference, but the noise signal comes about in this way in extended regions of the test object 10.

The reflections at the microstructure and at the material defects can be separated by the SAFT method. The microstructure noise exhibits a spatial static. The reflections at the microstructure are phase-correlated. The summation in the SAFT algorithm leads, nevertheless, to a relative attenuation of the reflections at the microstructure, since the grain boundaries reflect more weakly than do the material defects. If a random in-phase superposition of the amplitudes of a plurality of grain boundaries gives rise to an amplitude sum, the angle thereof is yet more strongly restricted. With increasing angular interval, the amplitudes increase more strongly because of material defects than the amplitudes effected by the grain boundaries.

By way of example, a test head 16 with a diameter of d=24 mm is used for the inventive method. According to the invention, the sound field of the test head 16 is considered in the SAFT algorithm. By contrast therewith, the size of the test head 16 is neglected in the known SAFT algorithm.

The detected signal results, in particular, from the reflected component of an ultrasonic pulse from sudden spatial changes in the wave resistance in the test object 10. These changes are interpreted as material defects when no design-dependent material boundaries or material transitions are present there. The detected signal contains only information relating to the amplitude and the travel time. Since the speed of sound in the material of the test object 10 is known, the spacing can also be determined from the travel time. The spatial distribution of the sound field and of the sensitivity of the test head 16 can be used to determine the location in a lateral direction.

The signals with the amplitude and the travel time that are detected along the path of the test head 16 are added up directly in terms of travel time with reference to the location in the test object 10. As a result of this locally correct assignment to the correct location, the amplitude sum of the signals that come from a specific location in the test object increases with each added signal by the amplitude thereof. However, the amplitudes depend on the position of the test head 16, and therefore on the relative position of the material defect 28 inside the sound field.

The mean value of the amplitude of a material defect without the directional effect is proportional to its reflectivity weighted by a factor k. The factor k is a value for the mean sensitivity along the path of the material defect 18 through the sound field of the test head 16. The detected amplitude can be sensibly assessed in this way.

In the case of the method in accordance with the invention, it is not individual detected amplitudes that are evaluated as a function of time, but the calculated spatial amplitude distributions. These can be reconstructed by the SAFT method. The calculated spatial amplitude distributions have a relatively high signal-to-noise ratio than the directly detected amplitudes. Material defects can be more easily identified in this way.

The method in accordance with the invention enables the spread of the application of the reflector assessment in accordance with the AVG method in the case of small amplitudes by a relative reduction in the noise such as would be possible even when use is made of wide test heads 16. This is based on the assumption that the small amplitude is to be ascribed to the slight size of the reflector. Consequently, even the slight directional effect of the reflector, which is to be ascribed to diffraction, has only a negligible influence on the detected amplitude.

The inventive method enables, in particular, the investigation of large test objects 10 with correspondingly large sound paths. These large sound paths cause the small amplitudes.

The inventive method can be applied to known classic test techniques in which the test object is scanned mechanically and the location or the movement of the test head 16 is known in relation to each detected amplitude/travel time diagram.

The assessment of the amplitude is performed by firstly scanning the reflector by the sound field. The angular dependence of the amplitude inside the sound field is known. m amplitudes are summed in a defined angular interval $\Delta\gamma$ about the acoustic axis. This yields a unique relationship between the amplitude sum $H_{Sum}$ and the size of a reference reflector that would generate the same amplitude sum $H_{Sum}$.

The amplitude sum $H_{sum}$ is given by:

$$H_{Sum}=\Sigma H_i(\gamma_i),$$

summing being performed over the number m of the detected amplitudes. Here, $H_i$ are the detected amplitudes for the individual measurements, and $\gamma_i$ is the angular spacing from the acoustic axis. Within a fixed spacing of the measurement points, the angular spacings are also approximately equidistant for the individual measurements. With increasing number m of the individual measurements, the correction factor k approaches a limiting value that corresponds to the mean sensitivity in the angular interval $\Delta\gamma$. The spacing between the material defect 18 and the test head 16 that is relevant for the AVG method is yielded from the position of the test head 16 when the specific location of the material defect 18 lies on the acoustic axis.

The following relationship exists between the amplitude sum $H_{Sum}$ and the amplitude $H_{AVG}$ in accordance with the AVG method:

$$H_{AVG}=H_{Sum}/(m*k),$$

m being the number of the individual measurements, and k a correction factor. The correction factor k is given by:

$$k=(1/m)\Sigma H_0(\gamma_i),$$

summing being performed over the number m of the detected amplitudes. Here, $H_0(\gamma_i)$ is the angle-dependent amplitude distribution in the sound field of the test head 16, which is normalized to $H_0(\gamma=0)=1$.

With increasing size of the material defect, that is to say the reflector, the directional effect thereof also increases. With relatively large material defects and given a mean inclined position, this can lead to an underassessment of the amplitude in the angular interval Δγ, and should therefore be considered. The method is particularly suitable for relatively small material defects whose directional effect is of relatively low importance.

Figure 4:
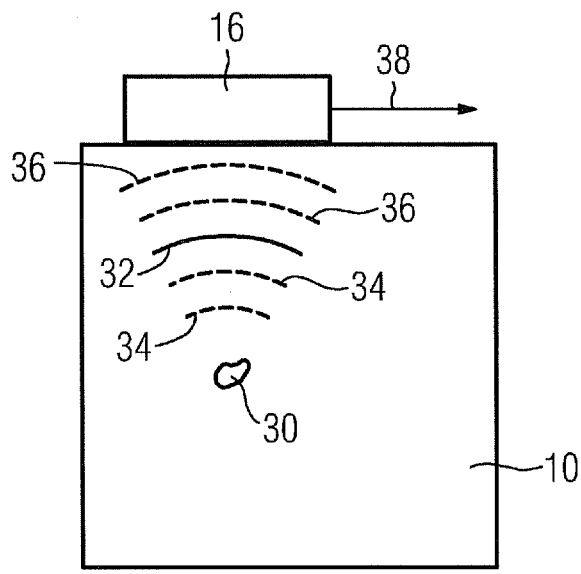
FIG. 4 shows a schematic sectional view of the test object and a focusing test head in accordance with the prior art.

FIG. 4 illustrates a schematic sectional view of the test object 10 and a focusing test head 16 in accordance with the prior art. The test object 10 has a material defect 30. Located on the outside of the test object 10 is the test head 16, which is designed as a focusing test head. Focussed sound waves 32, 34 and 36 are emitted by the test head 16.

Here, the continuous line illustrates the wave front of the current sound wave 32. The dashed lines illustrate the wave fronts of the earlier sound waves 34 and the later sound waves 36. The focused sound waves 32, 34 and 36 propagate along a predetermined direction with a laterally limited extent. The focused sound waves 18 and 20 thereby propagate in a non-spherical fashion in the entire half space.

During the scanning, the test head 16 moves on the surface of the test object 10 along a scanning direction 38. The focusing occurs only inside the near field of the test head 16, however. The greater the width of the test head 16 perpendicular to the direction of emission, the greater is the length of the near field, and thus the penetration depth of the focused sound waves 32, 34 and 36.

Figure 5:
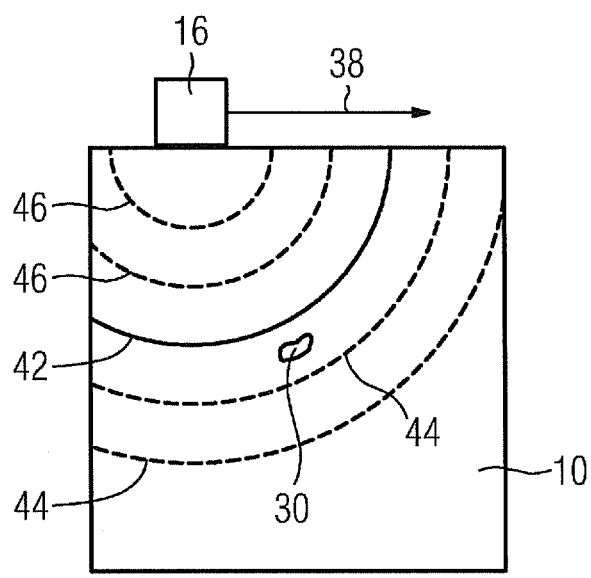
FIG. 5 shows a schematic sectional view of the test object and a test head in accordance with the SAFT method in accordance with the prior art.

FIG. 5 shows a schematic side view of the test object 10 and the test head 16 in the case of the SAFT method in accordance with the prior art. The test object 10 is illustrated with the material defect 30. The test head 16 is located on the outside of the test body 10. In comparison with FIG. 4, the test head 16 has a relatively small diameter and is not of focusing design.

Sound waves 42, 44 and 46 in the shape of spherical shells are emitted by the test head 16. The wave front of the current sound wave 42 in the shape of a spherical shell is illustrated by a continuous line. The dashed lines illustrate the wave fronts of the earlier sound waves 44 in the shape of spherical shells, and the later sound waves 46 in the shape of spherical shells. A comparison of FIG. 4 and FIG. 5 makes it clear that the wave fronts 32, 34 and 36, on the one hand, and 42, 44 and 46, on the other hand, are oppositely curved.

The test object 10 is subdivided into volume elements by a computer in the case of this SAFT method. Each volume element is considered sequentially as a reflector during scanning. The reflected signal components of various positions of the test head 16 that belong to the same volume element are recorded and added up in phase with the aid of the computer. Echo signals of large amplitude are obtained in this way only for such locations as have reflection based on constructive interference.

For locations without actual reflection, the echo signals are extinguished on the basis of destructive interference. In the case of constructive interference, the scanning and computing operation simulates an ultrasonic detector whose size corresponds to the scanned surface. In this known SAFT method, the insonification angle is always 0°, and the entire surface of the test object 10 is scanned.

In contrast therewith, in accordance with the invention the insonification angle α is variable.

The inventive method is not limited to the cylindrical test object 10 such as wheel disks or shafts. The insonification direction can be composed of suitable base vectors that are adapted to the geometric shape of the test object 10.

Furthermore, given a suitable selection of the swivel axes of the test head 16, it can suffice, moreover, not to need to scan the entire surface, but only along a predetermined segment or a predetermined path. The inventive method thus opens up a number of possibilities for detecting the entire volume of the test object 10 satisfactorily.

The inventive method leads to a substantial improvement in the detectability of small material defects and ones that are located deep in the interior of the test object 10.

The invention claimed is:

1. A method for nondestructive material testing of a sectionally solid test object by an application of ultrasonic waves to the test object and a detection of the ultrasonic waves reflected inside the test object, the method comprising:
    subdividing the test object into a plurality of predetermined volume elements using an aid of a computer;
    applying ultrasound to the test object at a plurality of surface elements while scanning a surface or a surface section of the test object;
    detecting the sound waves reflected at the plurality of volume elements while scanning the plurality of surface elements on the surface or on the surface section of the test object;
    adding, in-phase, the sound waves reflected at the plurality of volume elements and detected at the plurality of surface elements of the surface of the test object within a predetermined angular interval about the acoustic axis; and
    using an angle-dependent amplitude distribution in a sound field of a test head,
    wherein the angle-dependent amplitude distribution in a sound field of the test head is used to determine a plurality of amplitudes of the reflected sound waves, and
    wherein a specific number of amplitudes are summed with the predetermined angular interval about the acoustic axis in order to calculate a size of a reference reflector that would produce a same amplitude sum.

2. The method as claimed in claim 1, wherein the angle-dependent amplitude distribution is used to determine a correction factor that corresponds to a mean sensitivity along a path through the sound field of the test head.

3. The method as claimed in claim 1, wherein, in the adding, a plurality of amplitudes of the sound waves are added up in phase within the predetermined angular interval about the acoustic axis.

4. The method as claimed in claim 1, wherein the applying of ultrasound to the test object is performed at a plurality of insonification angles with reference to a surface element on the surface of the test object.

5. The method as claimed in claim 1,
    wherein the plurality of insonification angles lie within a cone, and
    wherein an axis of symmetry of the cone forms a normal to the respective surface element.

6. The method as claimed in claim 1, wherein the surface or the surface section of the test object is scanned along a predetermined line.

7. The method as claimed in claim 1, wherein the surface or the surface section of the test object is scanned in accordance with a predetermined scheme.

8. The method as claimed in claim 1, wherein the surface or the surface section of the test object is completely scanned.

9. The method as claimed in claim 1, wherein the plurality of insonification angles are in a range between 0° and 50°.

10. The method as claimed in claim 9, wherein the plurality of insonification angles are in the range between 0° and 30°.

11. The method as claimed in claim 1, wherein the test object is a sectionally rotationally symmetrical test object.

12. The method as claimed in claim 1, wherein the test object is a sectionally cylindrical test object.

13. The method as claimed in claim 12, wherein a insonification direction includes a radial, tangential and/or axial component with reference to the surface of the cylindrical test object.

14. The method as claimed in claim 1, wherein the test object is made from metal.

15. The method as claimed in claim 1, wherein the test object is a forged component.

16. The method as claimed in claim 1, wherein the test object is a turbine wheel.

17. A device for nondestructive material testing of a sectionally solid test object, comprising:
- a test head for the emission of a plurality of ultrasonic waves and for the detection of the plurality of ultrasonic waves reflected inside the test object,
- wherein the device is used to conduct a method for nondestructive material testing of a sectionally solid test object by an application of ultrasonic waves to the test object and a detection of the ultrasonic waves reflected inside the test object, the method comprising:
- subdividing the test object into a plurality of predetermined volume elements using an aid of a computer;
- applying ultrasound to the test object at a plurality of surface elements while scanning a surface or a surface section of the test object;
- detecting the sound waves reflected at the plurality of volume elements while scanning the plurality of surface elements on the surface or on the surface section of the test object; and
- adding, in-phase, the sound waves reflected at the plurality of volume elements and detected at the plurality of surface elements of the surface of the test object within a predetermined angular interval about the acoustic axis; and
- using an angle-dependent amplitude distribution in a sound field of a test head,
- wherein the angle-dependent amplitude distribution in a sound field of the test head is used to determine a plurality of amplitudes of the reflected sound waves, and
- wherein a specific number of amplitudes are summed with the predetermined angular interval about the acoustic axis in order to calculate a size of a reference reflector that would produce a same amplitude sum.

18. The device as claimed in claim 17, wherein the test head is swivel mounted such that an insonification direction is varied with reference to a first surface normal to a second surface of the test object.

19. The device as claimed in claim 18, wherein the test head is mounted to swivel between 0° and 60° with reference to the first surface.

* * * * *